(12) United States Patent
Hoffman et al.

(10) Patent No.: US 6,544,565 B2
(45) Date of Patent: *Apr. 8, 2003

(54) **USE OF *VALERIANA* FOR THE TREATMENT OF RESTLESS LEG SYNDROME AND RELATED DISORDERS**

(75) Inventors: Keith Hoffman, Del Mar, CA (US); Costas Loullis, Carlsbad, CA (US)

(73) Assignee: Ancile Pharmaceuticals, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/995,538

(22) Filed: Nov. 28, 2001

(65) Prior Publication Data

US 2002/0064569 A1 May 30, 2002

Related U.S. Application Data

(63) Continuation of application No. 09/475,494, filed on Dec. 30, 1999, now Pat. No. 6,346,283.
(60) Provisional application No. 60/126,534, filed on Mar. 26, 1999.

(51) Int. Cl.$^7$ .................. A61K 35/78; A61K 31/33; A61K 31/045
(52) U.S. Cl. .................. 424/733; 514/183; 514/906; 514/724; 514/729
(58) Field of Search .................. 424/733; 514/183, 514/906, 724, 729

(56) References Cited

U.S. PATENT DOCUMENTS 5,763,494 A 6/1998 Balandrin et al. .......... 514/629

FOREIGN PATENT DOCUMENTS

| WO | WO 97/39355 | 10/1997 |
|----|-------------|---------|
| WO | WO 98/08498 | * 3/1998 |

OTHER PUBLICATIONS

Boucher, M.A., Restless legs syndrome in home healthcare, *Home Healthcare Nurse*, Aug., 1997, 15(8):551–6.
Dooley, et al., *Premipexole, a review of its use in the management of early and advanced Parkinson's disease*, Drugs Aging, Jun. 1998, 12(6):495–514.
Fox, G.N., Restless leg syndrome, *American Family Physician*, Jan. 1986, 33(1):147–52.
Grandjean, P., Restless leg syndrome—current aspects, *Schweiz Rundsch Med. Prax.*, Apr. 1997, 30:86(18):732–6.
Hornyak, et al., Magnesium therapy for periodic leg movements–related insomnia and restless legs syndrome: an open pilot study, *Sleep*, Aug. 1998, 1:21(5):501–5.
Jones, et al., Restless legs syndrome—a review, *Eur. J. Vasc. Endovasc. Surg.*, Dec. 1997, 14(6):430–2.

Joy, M.S., Clonazepam: benzodiazepine therapy for the restless legs syndrome, *ANNA J.* Dec. 1997, 24(6):686–9.
Krueger, B.R., Restless Legs syndrome and periodic movements of sleep, *Mayo Clinic Proc.* Jul. 1990, 65(7):999–1006.
Mennini To, et al., In vitro study on the interaction of the extracts and pure compounds from valeriana officinalis roots with GABA, Benzodiazepine and Barbiturate receptors in rat brain Fitoterapia, vol. 64, No. 4, 1993, pp. 291–300.
Morazzoni P., et al. Valeriana officinalis: traditional use and recent evaluation of activity. Fitoterapa, vol. 66, No. 2, 1995, pp. 99–112.
O'Keeffe, S.T., Restless legs syndrome, a review, *Arch. Internal Medicince*, Feb. 1996, 156(3):243–8.
Shannon, et al., Efficacy of pramipexole, a novel dopamine agonist, as monotherapy in mild to moderate Parkingson's disease. The Pramipexole Study Group. *Neurology*, Sep. 1997, 49(3):724–8.
Trenkwalder, et al., Periodic limb movements and restless legs syndrome. *Neurol. Clinic*, Aug. 1996, 14(3):629–50.
Walters, A.S., Toward a better definition of the restless legs syndrome. The International Restless Legs Syndrome Study Group. *Mov. Disord.* Sep. 1995, 10(5):634–42.
Wermuth, L., A double–blind, placebo–controlled, randomized, multi–center study of pramipexole in advanced Parkinson's disease, *Eur. J. Neurol.*, May 1998, 5(3):235–242.
Wetter, et al., Restless legs and periodic leg movements in sleep syndromes, *J. Neurol.*, Apr. 1997, 244(4 Suppl. 1):S37–45.
Williams, D.C., Periodic limb movements of sleep and the restless legs syndrome, *Va. Med. Q.*, Fall 1996, 123(4):260–5.

* cited by examiner

Primary Examiner—Christopher R. Tate
(74) *Attorney, Agent, or Firm*—Knobbe Martens Olson & Bear

(57) ABSTRACT

A method of inhibiting at least one symptomology of Restless Leg Syndrome (RLS) and its related disorders, including disorders such as periodic limb movements in sleep (PLMS) and periodic limb movement disorder (PLMD), is disclosed. The method optionally comprising identifying a host, afflicted with Restless Leg Syndrome (RLS) and its related disorders; and administering to the host a pharmaceutically effective amount of Valeriana. A novel method of inhibiting at least one symptomology of Restless Leg Syndrome (RLS) and its related disorders is disclosed. The method may also be used to treat a host in order to diminish undesired limb movements, and may involve the administration of a particular compound, found in the above-mentioned extracts, preferably selected from the group consisting of 10(14)-Aromadendren-4-ol, 6,10(14)-Guaiadien-4-ol, Valerenal, Valerenol, Valerenic acid, Acetoxyvalerenic acid, Hydroxyvalerenic acid, mimetics thereof, and may involve the administration of a combinations of these particular compounds and mimetics thereof.

14 Claims, 5 Drawing Sheets

DOPAMINE D3 ACTIVE COMPOUNDS

10(14)-Aromadendren-4-ol 6,10(14)-Guaiadien-4-ol

| COMPOUND | R GROUP | R' GROUP |
|---|---|---|
| Valerenal | -H | -CHO |
| Valerenol | -H | -CH$_2$OH |
| Valerenic Acid | -H | -CO$_2$H |
| Acetoxyvalerenic Acid | -OAc | -CO$_2$H |
| Hydroxyvalerenic Acid | -OH | -CO$_2$H |

USE OF *VALERIANA* FOR THE TREATMENT OF RESTLESS LEG SYNDROME AND RELATED DISORDERS

RELATED APPLICATIONS

This application claims priority to provisional application serial No. 60/126,534 filed Mar. 26, 1999 and Con. application Ser. No. 09/475,494 filed Dec. 30, 1999, now U.S. Pat. No. 6,346,284.

BACKGROUND OF THE INVENTION

1. Field of the Invention

This invention relates to novel methods for treating Restless Leg Syndrome (RLS) also known of restless leys Syndrome, and related disorders, such as periodic limb movements in sleep (PLMS) and periodic limb movement disorder (PLMD), and for diminishing the occurrence of unwanted limb movements. Particularly, this invention relates to the use of Valeriana, and more particularly to an extract of *Valeriana officinalis* L., for diminishing the occurrence of unwanted limb movements, either associated with or unassociated with RLS and/or related disorders.

2. Description of the Related Art

The set of conditions known as Restless Leg Syndrome (RLS), also known as Ekbom's Syndrome following Ekbom's description of the syndrome in 1944, has been known since at least 1685 (Willis). RLS is a fairly common sensorimotor disorder, yet is not widely recognized by the medical profession or healthcare providers. It is characterized in that it typically gives the individual who suffers from RLS an unpleasant sensation in the legs at rest, causing what is often described as an irresistible desire to move, which generally alleviates the discomfort. (Jones and Deodra, 1997) Also typically, individuals afflicted with RLS experience indescribable crawling sensations in their legs that often occur at night and that are only relieved by moving the legs. (Boucher, 1997) Accordingly, RLS and its related disorders are thought to be a common cause of severe insomnia. (Fox, 1986) RLS is idiopathic in most patients, and has been identified as a presenting feature of iron deficiency, and is also common in uremia, pregnancy, diabetes mellitus, rheumatoid arthritis, and polyneuropathy. (O'Keeffe, 1996) PLMD and PLMS, disorders related to RLS, are characterized by episodes of jerking of the limbs, often during periods in which the individual is asleep, and sometimes during periods in which the individual is awake.

RLS affects millions of individuals, having an estimated prevalence of between 1% and 5%. (Wetter and Pollmacher, 1997) Indeed, at least mild symptoms of RLS have been reported to occur in up to 5% of the population of the United States. (O'Keeffe, 1996)

The formal criteria for diagnosis of RLS include: (i) symmetric or asymmetric dysesthesia of the lower, and sometimes also of the upper, extremities; (ii) dysesthesia are typically present at rest, and are especially prevalent at night; (iii) dysesthesia induce a need to move; (iv) movement gives relief, but only for a few seconds. Occasionally, the dysesthesia may be painful. Additional criteria include: (v) involuntary, rhythmic retraction movements occurring especially at night, and especially during sleep stages I and II; (vi) sleep is disrupted and superficial, followed by daytime fatigue. (Grandjean, 1997) Thus, clinical criteria for diagnosis include sleep disturbance, involuntary movements in sleep or wakefulness, a normal neurologic examination, a chronic clinical course, and, in some cases, a positive family history. (Trenkwalder et al., 1996) And the following four minimal criteria for diagnosis have been proposed: (1) desire to move the extremities, often associated with paresthesias/dysesthesias; (2) motor restlessness; (3) worsening of symptoms at rest with at least temporary relief by activity, and (4) worsening of symptoms in the evening or night. (Walters, 1995) The related disorders share some of these characteristics.

The underlying cause of RLS and its related disorders is not clearly known. However, it has been observed that the frequency of occurrence increases with advancing age. In most individuals with RLS, the results of complete blood cell counts and iron, ferritin, folate, and vitamin B12 levels are normal. No hematologic or chemical abnormalities are associated with individuals who experience periodic movements during sleep who also do not have RLS (Krueger, 1990).

Regarding the etiology of RLS and related disorders, pathophysiologically it has been reported that a malfunction of dopamine and opiate receptors in the central nervous system are associated with RLS and related disorders. (Grandjean, 1997) And while the precise aetiology of RLS and PLMS are unknown, it has been reported that periodic leg movements result from a suprasegmental disinhibition of descending inhibitory pathways. An evaluation of the efficacy of certain drugs revealed that, according to one study, the dopaminergic, adrenergic and opiate systems play a major role in the pathogenesis of RLS/PLMS. In spite of this association, therapy of RLS and PLMS remains symptomatic except for some secondary forms. (Wetter and Pollmacher, 1997) Indeed, one study has reported that "[w]hile the Dopamenergic CNS pathways have been thought to be the primary neurotransmitter involved, the opioids secondary, there is mounting evidence that the situation is far more complicated, that many neurotransmitters, including stimulating and inhibiting amino acids, play a part." (Williams, 1996)

Currently, RLS is typically treated by drugs such as clonazepam, narcotics, dopamine agonists, benzodiazipines, clonidine, gabepentin, (Joy, 1997; Wetter and Pollmacher, 1997; Trenkwalder et al., 1996) and magnesium (Homyak et al., 1998), and typically via oral administration. Currently, one popular pharmaceutical treatment of RLS in the United States is pramipexole, known by the trade name Mirapex, [available from Pharmacia and Upjohn] which has been reported to cause major side effects including insomnia, and dizziness. For example: "In pramipexole recipients with early disease, the most commonly experienced adverse events were nausea, dizziness, somnolence, insomnia, constipation, asthenia and hallucinations." (Dooley M, Markham A, Pramipexole. A review of its use in the management of early and advanced Parkinson's disease, Drugs Aging June 1998; 12(6):495–514); "The most common adverse events (<10%) were dizziness, insomnia, nausea, and postural hypotension." (Wermuth L, A double-blind, placebo-controlled, randomized, multi-center study of pramipexole in advanced Parkinson's disease, *Eur J Neurol* May 1998 5(3):235–242); "In the assessment of adverse events, nausea, insomnia, constipation, somnolence, and visual hallucinations occurred more frequently in the pramipexole treatment group compared with placebo patients." (Shannon K M, Bennett J P Jr, Friedman J H, Efficacy of pramipexole, a novel dopamine agonist, as monotherapy in mild to moderate Parkinson's disease. The Pramipexole Study Group. Neurology September 1997;49(3):724–8).

Therefore, there exists a need for an effective, alternative treatment and related treatment regime options for individuals who are afflicted with RLS and/or its related disorders. More particularly, there exists a need for treatments that do not induce the unwanted effects observed in modern therapeutics for Restless Leg Syndrome (RLS) and related disorders.

SUMMARY OF THE INVENTION

A novel method of inhibiting at least one symptomology of Restless Leg Syndrome (RLS) and its related disorders is disclosed. Said method comprises identifying a host afflicted with Restless Leg Syndrome (RLS) or a related disorder; and administering to said host a pharmaceutically effective amount of Valeriana. The Valeriana is preferably an extract, and more preferably an extract of *Valeriana officinalis* L. The host is preferably a mammal, and may also preferably be a canine, feline, or member of the Class Rodentia. The method of the present invention may be used to treat a host in order to diminish undesired limb movements, and may involve the administration of a particular compound, found in the above-mentioned extracts, preferably selected from the group consisting of 10(14)-Aromadendren-4-ol, 6,10(14)-Guaiadien-4-ol, Valerenal, Valerenol, Valerenic acid, Acetoxyvalerenic acid, Hydroxyvalerenic acid, and mimetics thereof, and may involve the administration of a combinations of these particular compounds and mimetics thereof.

BRIEF DESCRIPTION OF THE DRAWINGS

The accompanying drawings, which are incorporated in and form part of the specification, merely illustrate embodiments of the present invention. Together with the remainder of the specification, they are meant to serve to explain the principles of the invention to those of skill in the art. In the drawings.

DETAILED DESCRIPTION OF THE PREFERRED EMBODIMENT

Figure 1:
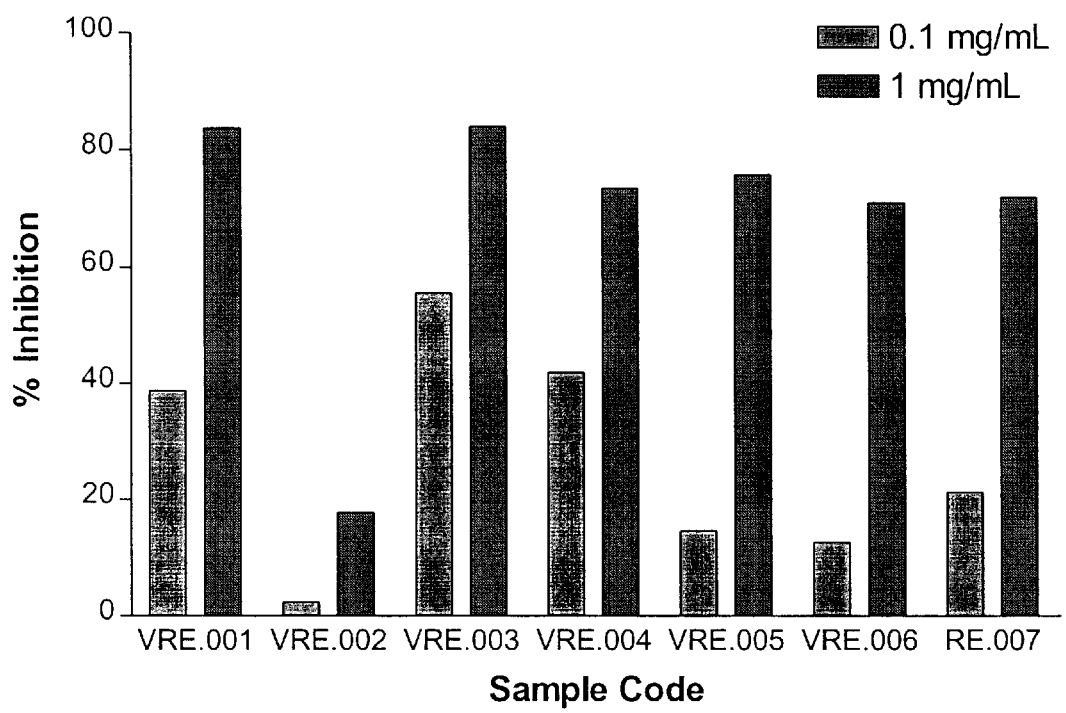
FIG. 1 illustrates a graphic depiction of the effect of commercially available Valerian extracts on binding to the peripheral benzodiazephine receptors according to the invention.

In a preferred embodiment, the present invention provides a natural plant extract, and particularly an extract of Valeriana, and more particularly an extract from *Valeriana officinalis* L., that affects the peripheral and central nervous system in a manner that alleviates the symptomologies of Restless Leg Syndrome (RLS) and related disorders. Further, the present invention provides the advantage of alleviating the symptomologies of RLS and related disorders without causing the side effects associated with benzodiazipine-type treatment, and other current treatment or treatments of, RLS and related disorders. The present invention provides the advantage of providing an alternative treatment option for RLS and related disorders, of which there is a need in the art.

Another advantage of the present invention, which includes the use of Valerian extract in the treatment of RLS and related disorders, is that extracts of Valeriana have not been shown to cause such side effects and therefore, the treatment of RLS with Valeriana may increase compliance for the RLS patient as well as address the specific problem of insomnia associated with RLS and/or other pharmaceutical treatments for RLS. These current treatments have a wide variety of negative side effects, which have been reported and detailed (Silber, 1997). Also, tolerance to the treatment can develop, causing the efficacy of a particular treatment regime to diminish with time. Also, rebound phenomena are associated with currently known treatments (Krueger, 1990; Homyak et al., 1998). Additionally, and as would be appreciated by one skilled in the art, current treatments such as benzodiazipines are associated with a host of unwanted effects such as memory loss, addiction potential, and other related side effects.

As used herein, the terms "Valeriana" and "valerian" each refer to any plant of the Valerianaceae, and therefore refers, at least to, the plant designated *Valeriana officinalis* L. This species includes all recognized subspecies of *Valeriana officinalis* L. Some of these subspecies are also commonly referred to, in alternative taxonomic systems, as: *Valeriana exaltata* J. C. Mikan, *Valeriana nitida* Kreyer, *Valeriana palustris* Wibel, *Valeriana wolgenis* Kazak, *Valeriana grossheimii* Vorosch, *Valeriana collina* Wallr, *Valeriana Rossica* P. A. Smim, *Valeriana spryngini* P. S. Smim, *Valeriana angustifolia* Tausch, *Valeriana tenuifolia* Vahl, *Valeriana wallrothii* Kreyer, *Valeriana ucrainica* Demjan, *Valeriana sambucifolia* J. C. Mikan, *Valeriana excelsa* Poir, and *Valeriana officinalis* L.subsp. excelsa (Poir.) Rouy. Plants of the species *Valeriana officinalis* L. may be characterized as follows: These plants grow from a short rhizome to 2 m high, flowers, and then die back again in the winter. These plants have pinnately-divided leaves with six to ten pairs of lance-shaped leaflets, and bear many small white or pink flowers in a dense head of several stalked clusters. The heads bare small (5 mm) tapered seeds.

As used herein, the term "root" or "roots" refers to all of subterranean portion of a specifically or generically identified plant, including, but not limited to, the roots, the rhizomes, and the stolons of the specifically or generically identified plant. Where the term "roots" is not modified by a specifically or generically identified plant, it will be understood that the term refers to the roots of the genus, and the various species, of Valeriana.

As used herein the term "Restless Leg Syndrome (RLS) and related disorders" means diseases, disorders, syndromes or conditions characterized by periodic limb movements such as periodic limb movements such as in sleep (PLMS) and periodic limb movement disorder (PLMD), and the treatment of such diseases, disorders, syndromes or conditions includes any pharmacological means of diminishing the occurrence of unwanted limb movements.

As used herein, the terms "reduces," "reduced," or "reducing," when used to refer to one or more symptomology of a disease, refers to any observable lessening of that characteristic when the method or composition of the present invention is compared to prior art methods or compositions.

As used herein, the terms "disorder" and "disease" refer to any disorder, disease, condition, syndrome or combination of manifestations or symptoms recognized or diagnosed as a disorder. If modified by reference to a particular disease or by reference one or more or a set of manifestations or symptoms, that usage of "disorder" or "disease" refers to any such disorder, disease, condition, syndrome or combination of such manifestations or symptoms recognized or diagnosed as a such disorder.

As used herein, the term "pharmaceutically effective amount" refers to an amount sufficient to alleviate, in any degree or manner, one or more of the manifestations or symptoms recognized or diagnosed as associated with the modifying disorder, the modifying manifestations, or the modifying symptom.

EXAMPLE 1

Effects of Valerian Extract on Peripheral and Central Nervous System

In Table 1, data are shown which demonstrate that an extract from *Valeriana officinalis* L. affected the peripheral and central nervous system in a manner consistent with alleviating one or more of the symptomologies of Restless Leg Syndrome (RLS) and related disorders. All bio-assays, except the Rat A1, were performed at the following laboratory according to standard methods known to those skilled in the art:

Panlabs Taiwan, Ltd., 158 Li-The Road, Peitou, Taipei, Taiwan, R.O.C.

Two examples of suitable assay procedures are as follows:

Human D3 Assay: This assay measures binding of [$^3$H]-Spiperone to human dopamine D3 receptors. CHO cells stably transfected with a plasmid encoding the human dopamine D3 receptor were used to prepare membranes in modified Tris-HCl pH 7.4 buffer using standard techniques. A 10 mg aliquot of membrane was incubated with 2 nM [$^3$H]-Spiperone for 120 minutes at 37° C. Non-specific binding was estimated in the presence of 25 $\mu$M S-(-)-sulpiride. Membranes were filtered and washed three times and the filters are counted to determine the amount of [$^3$H]-Spiperone specifically bound. Compounds were screened at 10 $\mu$M.

Human A1 Assay: This assay measures binding of [$^3$H]-DPCPX to adenosine A1 receptors. CHO cells stably transfected with a plasmid encoding the human adenosine A1 receptor were used to prepare membranes in modified HEPES pH 7.4 using standard techniques. A 10 mg aliquot of membrane was incubated with 1 nM [$^3$H]-DPCPX for 90 minutes at 25° C. Non-specific binding was estimated in the presence of 100 $\mu$M R(-)-PIA. Membranes were filtered and washed three times and the filters were counted to determine [$^3$H]-DPCPX specifically bound. Compounds were screened at 10 $\mu$M.

Rat adenosine A1 receptor binding assays were performed at the following laboratory according to standard methods known to those skilled in the art:

Oceanix Biosciences, 7170 Standard Drive, Hanover, M.d. 21076

Rat A1 Assay: This assay measures binding of [$^3$H]-8-Cyclopentyl-1,3-dipropylxanthine to adenosine A1 receptors. Rat cortical membranes, prepared using standard techniques, were used as a source of the receptor. Reactions were carried out in 50 mM TRIS-HCl (pH 7.7) for 60 minutes at 25° C. Non-specific binding was estimated in the presence of 10 $\mu$M 2-chloroadenosine. The reaction was terminated by rapid vacuum filtration onto glass fiber filters. Radioactivity trapped onto the filters was determined and compared to control values in order to ascertain any interactions of test compound with the adenosine A1 binding site.

Figure 2:
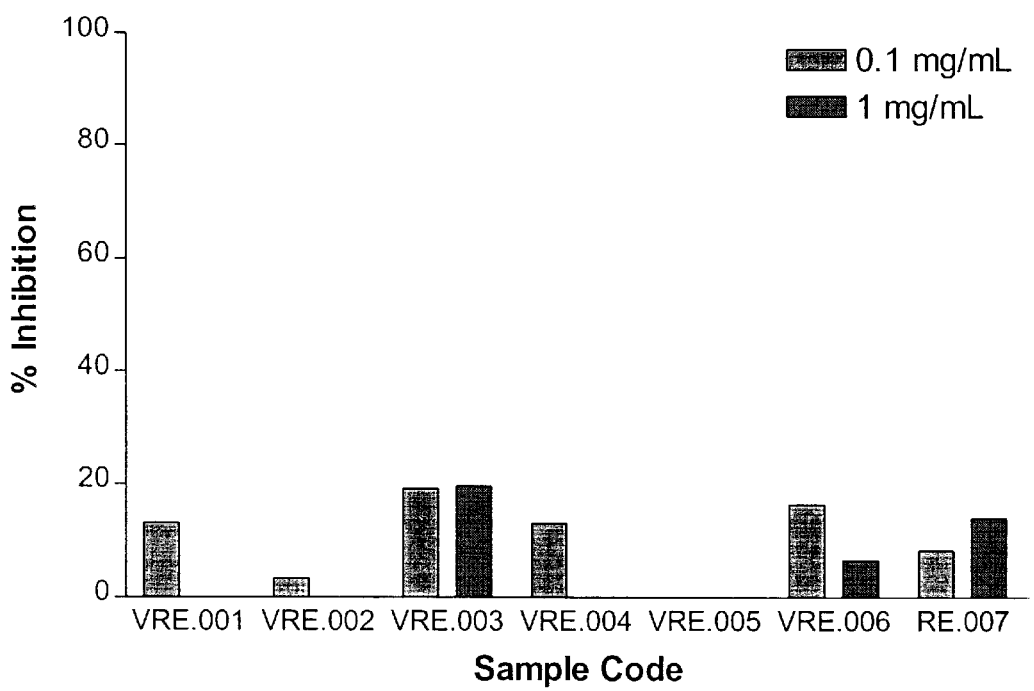
FIG. 2 illustrates a graphic depiction of the lack of effect of commercially available Valerian extracts on binding to the central benzodiazephine receptors according to the invention.

It has further been demonstrated, through in vitro binding tests, that extracts of *Valeriana officinalis* L., produced according to the method described in U.S. patent application Ser. No. 09/358,375, filed Jul. 21, 1999, and entitled "Process for the Extraction of Valerian Root," the entire contents of which are incorporated herein by reference, favorably interact with certain Central Nervous System (CNS) receptors, for example, the GABA, Adenosine, and Dopamine receptors. Such bind would explain the calming action of said extracts (see Table 1). In contrast, the CNS binding site associated with benzodiazepines was not affected by said Valerian extracts (see FIGS. 1 and 2). The results depicted in FIG. 2 indicate, via an in vitro model, that extracts of *Valeriana officinalis* L. will not result in the problematic side effects and side effect profiles associated with currently available benzodiazepine-type drugs. Additionally, as demonstrated by the data depicted in FIG. 1, extracts of *Valeriana officinalis* affect the binding of peripheral benzodiazepine receptors. Thus, is it believed, although the invention is not limited by any theory or hypothesis, that the peripheral benzodiazepine receptors mediate the activity of mitochondria in muscle cells, and thereby effect muscle activity (see FIGS. 1 and 2), and therefore mediate muscle calming.

TABLE 1

Percent Inhibition of Various Extract Fractions Against Various Receptors

| | % Inhibition | | | | | | | | |
|---|---|---|---|---|---|---|---|---|---|
| | VRE. 001 | VRE. 002 | VRE. 003 | VRE. 004 | VRE. 005 | VRE. 006 | RE. 007 | Mean | SD |
| A1 Human | | | | | | | | | |
| 0.1 mg/mL | −10 | −9 | 17 | 14 | −12 | −9 | 8 | −0.14 | 12.62 |
| 1 mg/mL | 38 | −9 | 60 | 47 | 28 | 32 | 23 | 31.29 | 21.68 |
| A1 Rat | | | | | | | | | |
| 0.1 mg/mL | 43.85 | 12.64 | 11.36 | 28.45 | 21.86 | 20.57 | 22.76 | 23.07 | 10.91 |
| 1 mg/mL | 84.69 | −7.28 | 47.93 | 76.01 | 60.56 | 42.77 | 52.81 | 51.07 | 29.80 |

TABLE 1-continued

Percent Inhibition of Various Extract Fractions Against Various Receptors

| | % Inhibition | | | | | | | | |
|---|---|---|---|---|---|---|---|---|---|
| | VRE. 001 | VRE. 002 | VRE. 003 | VRE. 004 | VRE. 005 | VRE. 006 | RE. 007 | Mean | SD |
| BDZ Central | | | | | | | | | |
| 0.1 mg/mL | 13.08 | 3.32 | 19.23 | 13.01 | −1.9 | 16.4 | 8.26 | 10.20 | 7.46 |
| 1 mg/mL | −42.73 | −11.31 | 19.61 | −31.61 | −13.73 | 6.57 | 13.98 | −8.46 | 23.32 |
| BDZ Peri | | | | | | | | | |
| 0.1 mg/mL | 38.83 | 2.32 | 55.5 | 41.86 | 14.66 | 12.63 | 21.19 | 26.71 | 19.04 |
| 1 mg/mL | 83.64 | 17.82 | 83.85 | 73.33 | 75.71 | 70.84 | 71.73 | 68.13 | 22.82 |
| Cl Channel | | | | | | | | | |
| 0.1 mg/mL | 12.58 | −33.05 | 11.7 | 3.81 | 1.79 | 9.45 | −6.09 | 0.03 | 15.98 |
| 1 mg/mL | 98.15 | 14.66 | 40.02 | 86.72 | 91.95 | 49.34 | 10.46 | 55.90 | 36.73 |
| D1 | | | | | | | | | |
| 0.1 mg/mL | 13.52 | 24.52 | 43 | 8.95 | 5.36 | 37.64 | 14.48 | 21.07 | 14.50 |
| 1 mg/mL | 70.25 | 34.88 | 37.78 | 36.55 | 68.16 | 49.22 | 23.44 | 45.75 | 17.69 |
| GABA-A | | | | | | | | | |
| 0.1 mg/mL | 94.5 | 61.56 | 83.24 | 91.89 | 90.49 | 89.53 | 36.16 | 78.20 | 21.61 |
| 1 mg/mL | 93.24 | 95.62 | 97.56 | 91.37 | 100.13 | 96.79 | 59.73 | 90.63 | 13.92 |
| GABA-B | | | | | | | | | |
| 0.01 mg/mL | 26 | 13 | −10 | 46 | 12 | 7 | −6 | 12.57 | 19.08 |
| 0.1 mg/mL | 82 | 14 | 28 | 66 | 77 | 53 | 4 | 46.29 | 31.14 |
| 1 mg/mL | 102 | 96 | 81 | 116 | 105 | 110 | 48 | 94.00 | 23.14 |

EXAMPLE 2

Process for Preparing a Valerian Extract

As a further non-limiting, preferred example, an extract of the plant *Valeriana officinalis* and specifically, of its roots, wherein the amount of valepotriates in the extract is reduced below a detectable level, may be obtained, in a manner consistent with that described in U.S. patent application Ser. No. 09/358,375, filed Jul. 21, 1999, and entitled "Process for the Extraction of Valerian Root," the entire contents of which are herein incorporated by reference, by performing the follow steps, in the following sequence. As will be appreciated by those of skill in the art, such a process yields an extract possessing the following compounds as constituents: 10(14)-Aromadendren-4-ol, 6,10(14)-Guaiadien-4-ol, Valerenal, Valerenol, Valerenic acid, Acetoxyvalerenic acid, Hydroxyvalerenic acid. Additionally, mimetics of these constituents will possess certain similar biological properties as the identified constituents, and combinations of these constituents, including combination of these constituents and mimetics thereof, may be employed within the meaning of the present invention.

(1) At an extraction facility the *Valeriana officinalis* L. rhizome, roots, and stolons (Valerian biomass) are prepared for extraction by chipping in a hammermill with an appropriate screen installed for sizing. The chipped Valerian biomass is analyzed to ensure that at least 85% passes through a Tyler 20-mesh screen. The chipped Valerian biomass is packaged in a polyethylene container, doubly lined with polyethylene bags, and closed with a polyethylene lid.

(2) The chipped Valerian biomass is added to an extraction solvent in a ratio of 1 kg of chipped Valerian biomass to 5L of extraction solvent, then stirred. The extraction solvent consists of a mixture of 70% denatured ethanol (95% ethanol+5% methanol) and 30% potable water by volume. The mixture is stirred and heated to reflux (77–80° C.) for at least 5, or approximately 6, 7, 8, or 10 hours to reduce the levels of valepotriates by a target of not less than 95% from the level initially found in the extraction mixture, and to a low as undetectable levels. The mixture is cooled below reflux (approximately 40–50° C., or more particularly 42, 45, and 47° C.) and the solids are filtered from the liquid. The extraction vessel and the solids in the filter are rinsed with the same solvent solution as used for extraction. The rinse consists of 2 L of solvent solution for each 1 kg of chipped Valerian biomass extracted. The filtrate containing the extracted material is concentrated to an oily consistency under reduced pressure at approximately 50° C., or approximately 45° C. or 55° C., to a final volume of approximately 0.16L for each 1 kg of chipped Valerian root extracted.

3) Optionally, the concentrate is mixed with an acceptable chemical base, to reduce the odor of the extract, as described in U.S. Provisional Application No. 60/255,765, entitled "Process For The Reducing The Odor of Valeriana," and filed herewith, the entire contents of which are hereby incorporated by reference herein.

(4) The concentrate is mixed with an excipient (maltodextrin) to facilitate drying. The final maltodextrin concentration by weight will be between 20–25% of the botanical drug substance.

5) The mixture of concentrate and excipient is dried under a reduced pressure of 28–30 inches Hg, gauge, and a temperature of 40–50° C., or more particularly 42, 45, and 47° C., until the water content is 5% or less, or 10% or less, or 2.5% or less, by Karl Fisher analysis. The dried extract on excipient is milled to a target of 90% passing through an 80-mesh screen.

(6) The final powder is packaged in 60 L capacity containers constructed of High Density Polyethylene (HDPE). The containers are double lined with Low Density Polyethylene (LDPE) bags that contain no dye and are extruded from virgin polymer only. Twisting the excess bag closed at the open end and securing it with an elastic band closes each bag within the packaging container. These containers have a HDPE lid with a gasket seal to the container. The lid is secured to the container with an aluminum clamp band. The clamp band is secured with a non-removable security seal.

Said extract, or other extracts of Valeriana, obtained via methods that are appreciated by those skilled in the art, are administered to a host, said host having been identified as afflicted with Restless Leg Syndrome and related disorders, in a pharmaceutically effective amount.

Furthermore, said extract, or other extracts of Valeriana, obtained via the above-described method may be, as will be appreciated by those skilled in the art, administered to a host, preferably a mammalian host, and most preferably a canine, a feline, a rodent, (include a murine), or a human host, said host having been identified as suffering from or afflicted with undesired limb movements associated with Restless Leg Syndrome (RLS) or a related disorder. As will be appreciated by those of skill in the art, the above-described extract is preferably delivered in a pharmaceutically effective amount that does not induce unwanted side effects The extract produced, and preferably the tablets produced according to the methods of the present invention advantageously may be administered to an individual in a dose containing a pharmaceutically-effective amount of Valerian, Valerian extract, or component(s) therein. This administration can be through any effective route. It is contemplated that administration may be effected, for example, preferably orally, but also may also be administered intramuscularly, subcutaneously, intraperitoneally, transdermally, transmucosally, buccally, or through inhalation or pulmonary infusion. Dosages that are contemplated for a 70 kg adult human range from a lower limit of 10, 25, 50, 100, 150, 200, or 250 mg to an upper limit of 750, 1000, 1500, 2000, 2500, 3000, 4000, 5000, or up to 10,000 mg. of the compositions described herein, or other extracts of valerian. Preferred dosages for a 70 kg human are from about 100, 200, or 250 mg to about 1000, 1500, 2000, or 2500 mg. These dosages can be administered once, twice or up to four times per day, or two or more dosages may be combined. The dose may also be tailored to achieve a desired effect, but will depend on such factors as weight, diet, concurrent medication and other factors which those skilled in the medical arts will recognize.

The present invention also encompasses pharmaceutical compositions comprising a pharmaceutically acceptable carrier prepared for storage and subsequent administration, which have a pharmaceutically effective amount of the extract disclosed above in a pharmaceutically acceptable carrier or diluent. Acceptable carriers or diluents for therapeutic use are well known in the pharmaceutical art, and are described, for example, in Remington's Pharmaceutical Sciences, Mack Publishing Co. (A. R. Gennaro edit. 1985). Preservatives, stabilizers, dyes and even flavoring agents may be provided in the pharmaceutical composition. For example, sodium benzoate, sorbic acid and esters of p-hydroxybenzoic acid may be added as preservatives. In addition, antioxidants and suspending agents may be used.

These compositions may be formulated and used as, preferably, tablets, and also as capsules for oral administration. Suitable additional excipients are, for example, water, saline, dextrose, mannitol, lactose, lecithin, albumin, sodium glutamate, cysteine hydrochloride, and the like. In addition, if desired, the pharmaceutical compositions may contain relatively small amounts of nontoxic auxiliary substances, such as wetting agents, pH buffering agents, and the like.

In practicing the compositions of the invention, the formulated dosage may be used alone or in combination with other therapeutic or diagnostic agents. These products can be utilized in vivo, ordinarily in a mammal, preferably in a human, or in vitro. In employing them in vivo, the products or compositions can be administered to the mammal in any of a variety of manners known to persons skilled in the art, and may employ any of a variety of dosage forms.

EXAMPLE 3

Interaction of Valerian Root Extracts and Fractions of Valerian Root Extract with Human Dopamine D3 Receptors It has also been discovered, according to the present invention, that Valerian extracts demonstrate specificity for the Dopamine D3 subtype versus the other Dopamine receptors. Without being bound to a particular theory or action or functional hypothesis, it is believed that Mirapex (pramipexole), noted above, acts on the D3, D2, D4 receptor subtypes, and that Valerian's relative selectivity for the D3 subtype may be responsible for Valerian's lower incidence of side-effects relative to Mirapex.

TABLE 2

Effect of Valerian on ligand binding to human recombinant dopamine receptors.
(The ligand used was $^3$H-SCH-23390 in the dopamine $D_1$ assay and $^3$H-Spiperone in all other assays.)

| Receptor | Assay # | N = | Conc. μg/mL | % Inhibition |
|---|---|---|---|---|
| Dopamine $D_1$ | 1 | 2 | 1000 | 36 |
| | 1 | 2 | 100 | −8 |
| | 1 | 2 | 10 | −2 |
| | 2 | 3 | 1000 | 69 |

TABLE 2-continued

Effect of Valerian on ligand binding to human
recombinant dopamine receptors.
(The ligand used was $^3$H-SCH-23390 in the dopamine $D_1$ assay and
$^3$H-Spiperone in all other assays.)

| Receptor | Assay # | N = | Conc. μg/mL | % Inhibition |
|---|---|---|---|---|
| Dopamine $D_{2L}$ | 1 | 2 | 1000 | 19 |
| | 1 | 2 | 100 | 2 |
| | 1 | 2 | 10 | −10 |
| Dopamine $D_{2S}$ | 1 | 2 | 1000 | 26 |
| | 1 | 2 | 100 | −2 |
| | 1 | 2 | 10 | 6 |
| Dopamine $D_3$ | 1 | 2 | 1000 | 77 |
| | 1 | 2 | 100 | 13 |
| | 1 | 2 | 10 | 6 |
| | 2 | 4 | 2000 | 82 |
| | 2 | 4 | 1000 | 49 |
| | 2 | 4 | 500 | 24 |
| | 2 | 4 | 250 | 17 |
| | 2 | 4 | 125 | 6 |
| | 2 | 4 | 62.5 | 7 |
| | 2 | 4 | 31.25 | 4 |
| Dopamine $D_{4.2}$ | 1 | 2 | 1000 | 19 |
| Dopamine $D_{4.4}$ | 1 | 2 | 1000 | −15 |
| | 1 | 2 | 100 | −8 |
| | 1 | 2 | 10 | 10 |
| Dopamine $D_{4.7}$ | 1 | 2 | 1000 | 0 |

This example demonstrates the interaction of Valerian and fractions prepared from Valerian with human dopamine D3 receptors in vitro.

Low doses of dopamine D3 receptor agonists have been shown to increase slow wave sleep (SWS) and rapid eye movement (REM) sleep in animal models. Dopamine D3 agonists also reduce locomotor activity in rats. Studies indicate that treatment with a specific D3 agonist does not directly induce the release of dopamine. This suggests that the direct interaction of agonists with the dopamine D3 receptor is involved in the induction of sleep.

Aqueous and hydroalcoholic extracts of *Valeriana officinalis* L. (valerian) roots are commonly used as sedative agents. To understand the mechanism of this pharmacological activity, we investigated the effect of Valerian on ligand binding to the human dopamine D3 receptor. Fractions prepared from such extracts were also tested for interaction with dopamine D3 receptors to identify individual compounds, or classes of compounds, that may be partially responsible for the sedative action of Valerian.

Figure 4:
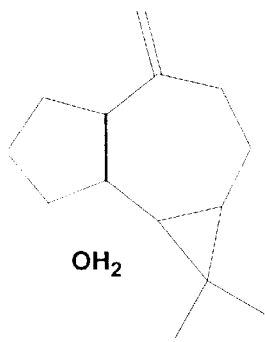
FIG. 4 illustrates the chemical structures of five structurally related compounds determined to be active in a dopamine D3 bio-assay according to the invention.
Figure 4:
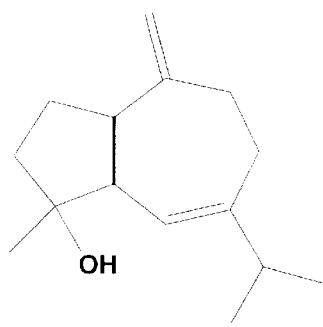
Figure 4:
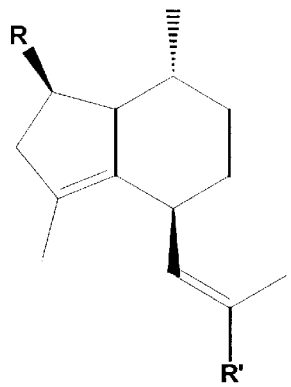
Figure 5:
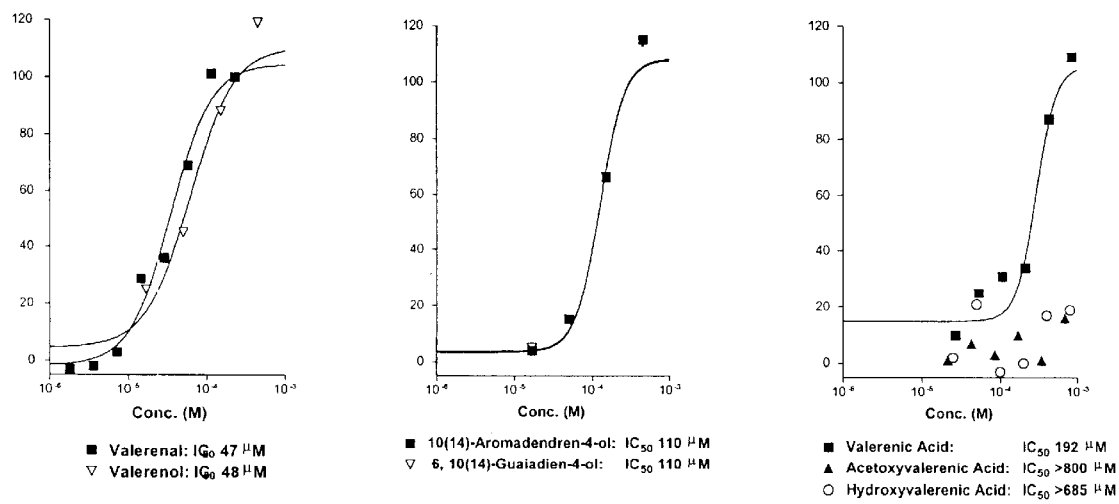
FIG. 5 illustrates the inhibition of ligand binding to the human dopamine receptor by various compounds isolated from Valerian according to the invention.

Materials and methods used in performing this example were as follows:

Valerian was subjected to the fractionation scheme schematically depicted in FIG. 4.

As the source of, and to isolate the receptors used in the example, membranes prepared from Chinese hamster ovarian (CHO) cells, stably transfected with a plasmid encoding the human dopamine D3 receptor, were used.

Sample preparation: Stock solutions of the valerian root extract were prepared by dissolving in 50% ethanol/water followed by sonication and filtration (0.45 μm) or by dissolving in 100% DMSO. Valerian fractions were dissolved in 100% DMSO. Prior to analysis, stock solutions were diluted in appropriate buffer. In each assay, the final ethanol or DMSO concentration was less than or equal to 1%.

Receptor binding assays: Standard receptor binding assays were performed at the following analytical laboratory: Panlabs Taiwan, Ltd., 158 Li-The Road, Peitou, Taipei, Taiwan, R.O.C. The assay method, based on the assay described in Sokoloff, P., Giros, B., Martres, M.-P., Bouthenet, M.-L. and Schwartz, J.-C. Molecular cloning and characterization of a novel dopamine receptor (D3) as a target for neuroleptics. Nature 347: 146–151, (1990), was as follows: The assay measures binding of [$^3$H] Spiperone to human dopamine D3 receptors. CHO cells stably transfected with a plasmid encoding the human dopamine D3 receptor are used to prepare membranes in modified Tris-HCl pH 7.4 buffer using standard techniques. A 10 mg aliquot of membrane is incubated with 2 nM [$^3$H]-Spiperone for 120 minutes at 37° C. Non-specific binding is estimated in the presence of 25 μM S-(-)-sulpiride. Membranes are filtered and washed 3 times and the filters are counted to determine [$^3$H]-Spiperone specifically bound. Compounds are screened at 10 μM. Results were as follows: Kd=0.12 nM; Bmax=1.9 pmol/mg protein; Specific Binding=85%. The Reference Data were as depicted in the following table, Table 3:

TABLE 3

Reference Data For Recptor Binding Assay
Reference Data:

| Compound | $IC_{50}$ (nM) | Ki (nM) | nH |
|---|---|---|---|
| R-(-)-Apomorphine | 270 | 15 | 0.9 |
| (+)-Butaclamol | 13 | 0.73 | 1.0 |
| Chlorpromazine | 38 | 2.1 | 0.9 |
| Clozapine | 4,200 | 240 | 1.0 |
| Dopamine | 1,100 | 64 | 0.9 |
| cis-Flupenthixol | 0.83 | 0.047 | 0.9 |
| Haloperidol | 26 | 1.5 | 1.2 |
| SCH-23390 | >10,000 | — | — |
| SKF-38393 | >10,000 | — | — |
| *Spiperone | 0.7 | 0.04 | 1.0 |
| S-(-)-Sulpiride | 850 | 48 | 1.0 |

*Indicates standard reference agent used.

SCH-23390=7-Chloro-2,3,4,5-tetrahydro-3-methyl-5-phenyl-1H-3-benzazepine-7-ol; SKF-38393=2,3,4,5-Tetrahydro-7,8-dihydroxy-1-phenyl-1H-3-benzazepine HCl.

Valerian root extract has been reported to posses sedative activity, presumably through the interaction of one or more of its constituents with receptors mediating sedation. The neuromodulator, dopamine, is a suspected sleep-inducing factor through its specific interaction with dopamine receptors. While there are a number of known dopamine receptor subtypes, activation of the dopamine D3 receptor is most closely associated with dopamine's sleep-inducing and sedative effects. This has been demonstrated with agents that selectively activate the D3 receptor. Studies indicate D3 selective agonists induce both slow wave sleep (SWS) and rapid eye movement (REM) sleep in rats.

To understand Valerian's mechanism of action, Valerian was tested in this example for its ability to displace radio-labeled ligand ($^3$H-spiperone) from the human dopamine D3 receptor in vitro. The data from the testing of Valerian at various concentrations on different days is summarized below in Table 4. The results indicate that Valerian root extract interacts with dopamine D3 receptors in a concentration-dependent manner.

TABLE 4

Interaction of Valerian extract with Human Dopamine D3 Receptors

| Experiment No. | Concentration | N | % Inhibition |
|---|---|---|---|
| 1 | 10 µg/mL | 2 | 6 |
|   | 100 µg/mL | 2 | 13 |
|   | 1000 µg/mL | 2 | 77 |
| 2 | 31.3 µg/mL | 4 | 4 |
|   | 62.5 µg/mL | 4 | 7 |
|   | 125 µg/mL | 4 | 6 |
|   | 250 µg/mL | 4 | 17 |
|   | 500 µg/mL | 4 | 24 |
|   | 1000 µg/mL | 4 | 49 |
|   | 2000 µg/mL | 4 | 82 |
| 3 | 100 µg/mL | 2 | 24 |
|   | 500 µg/mL | 2 | 36 |

Figure 3:
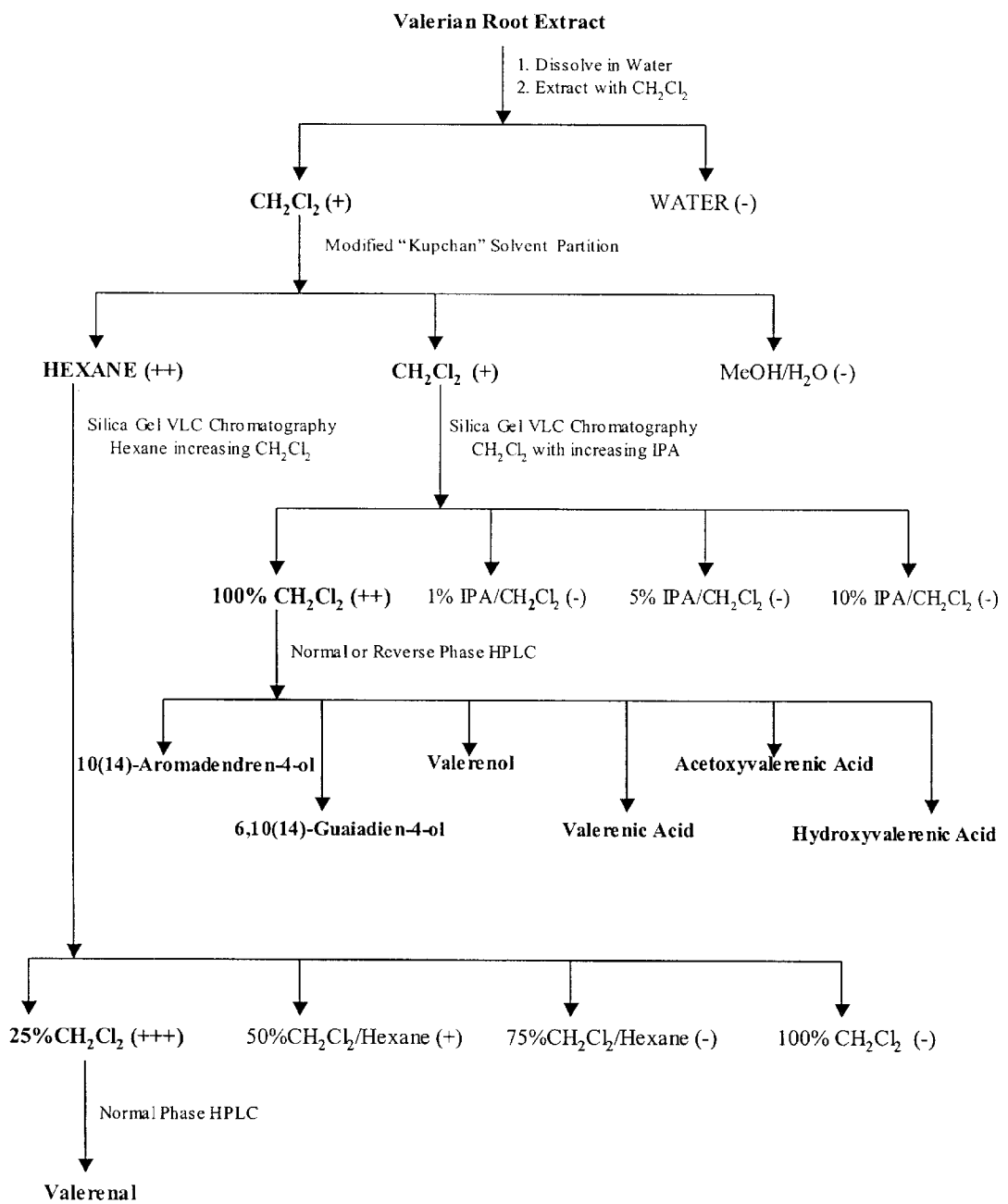
FIG. 3 illustrates a schematic Valerian fraction flow diagram including an exemplary isolation scheme used to assay dopamine D3 receptor binding activity.

In order to identify compounds or class of compounds from valerian root extract that interact with the dopamine D3 receptor, Valerian was subjected to bioactivity-guided fractionation (see FIG. 3). Valerian fractions were tested to determine their activity against the dopamine D3 receptor and active fractions were subjected to further sub-fractionation. The results from the testing of Valerian fractions and sub-fractions at various concentrations are summarized in Tables 5, 6, 7, and 8. These results indicate that several sub-fractions interact strongly with the receptor. Without being bound to any particular theory of action for the invention, the results of this example indicate that more than one compound may be responsible for the observed interaction of Valerian with the dopamine D3 receptor.

TABLE 5

Interaction of Valerian Fractions and Sub-fractions with Human Dopamine D3 Receptors

| | | % Inhibition | |
|---|---|---|---|
| Sample | Description | 500 µg/mL | 100 µg/mL |
| BKC-007-26-F0 | Valerian extract | 36 | 24 |
| BKC-007-26-F1 | $CH_2Cl_2$ soluble portion of BKC-007-26-F0 | 108 | 86 |
| BKC-007-26-F2 | Butanol soluble portion of BKC-007-26-F0 | 37 | 8 |
| BKC-007-26-F3 | Water soluble portion of BKC-007-26-F0 | -3 | 6 |
| BKC-007-26-F4 | Hexane soluble portion of BKC-007-26-F1 | 100 | 100 |
| BKC-007-26-F5 | $CH_2Cl_2$ soluble portion of BKC-007-26-F1 | 65 | 55 |
| BKC-007-26-F6 | Methanol soluble portion of BKC-007-26-F1 | 64 | -6 |
| BKC-007-26-F7 | Water elution of C18 column of BKC-007-26-F3 | 5 | -16 |
| BKC-007-26-F8 | Organic elution of C18 column of BKC-007-26-F3 | 11 | -20 |

TABLE 6

Interaction of Valerian Fractions and Sub-fractions with Human Dopamine D3 Receptors

| | | % Inhibition | |
|---|---|---|---|
| Sample | Description | 100 µg/mL | 20 µg/mL |
| KL-015-01-F1 | $CH_2Cl_2$ soluble portion of Valerian extract | 88 | 33 |
| KL-015-01-F4 | Hexane soluble portion of KL-015-01-F1 | 104 | 26 |
| KL-015-08-F1 | Silica Gel VLC fraction of KL-015-01-F4 | 79 | 36 |
| KL-015-08-F2 | Silica Gel VLC fraction of KL-015-01-F4 | 91 | 46 |
| KL-015-08-F3 | Silica Gel VLC fraction of KL-015-01-F4 | 89 | 42 |
| KL-015-08-F4 | Silica Gel VLC fraction of KL-015-01-F4 | 23 | 16 |
| KL-015-08-F5 | Silica Gel VLC fraction of KL-015-01-F4 | 5 | 19 |
| KL-015-08-F6 | Silica Gel VLC fraction of KL-015-01-F4 | -9 | 2 |
| KL-015-01-F5 | $CH_2Cl_2$ soluble portion of KL-015-01-F1 | 76 | 30 |
| KL-015-03-F1 | Silica Gel VLC fraction of KL-015-01-F5 | 22 | 22 |
| KL-015-03-F2 | Silica Gel VLC fraction of KL-015-01-F5 | 106 | 34 |
| KL-015-03-F3 | Silica Gel VLC fraction of KL-015-01-F5 | 113 | 42 |
| KL-015-03-F4 | Silica Gel VLC fraction of KL-015-01-F5 | 102 | 54 |
| KL-015-03-F5 | Silica Gel VLC fraction of KL-015-01-F5 | 56 | 18 |

TABLE 7

Interaction of Valerian Sub-fractions with Human Dopamine D3 Receptors

| | | % Inhibition | | |
|---|---|---|---|---|
| Sample | Description | 100 µg/mL | 50 µg/mL | 25 µg/mL |
| KL-015-01-F4 | Hexane soluble portion of KL-015-01-F1 | ND | 58 | 22 |
| KL-015-10-F1 | Silica Gel Column Fraction of KL-015-03-F2 | 122 | 74 | 49 |
| KL-015-14-F3 | Silica Gel Column Fraction of KL-015-08-F1 | 126 | 92 | 85 |
| KL-015-19-F1 | Silica Gel Column Sub-Fraction of Pooled Active Fractions from Previous Steps | 98 | 56 | 51 |
| KL-015-19-F2 | Silica Gel Column Sub-Fraction of Pooled Active Fractions from Previous Steps | 19 | 14 | 13 |
| KL-015-19-F3 | Silica Gel Column Sub-Fraction of Pooled Active Fractions from Previous Steps | 70 | 55 | 31 |
| KL-015-19-F4 | Silica Gel Column Sub-Fraction of Pooled Active Fractions from Previous Steps | 86 | 44 | 22 |
| KL-015-19-F5 | Silica Gel Column Sub-Fraction of Pooled Active Fractions from Previous Steps | 98 | 52 | 30 |
| KL-015-19-F6 | Silica Gel Column Sub-Fraction of Pooled Active Fractions from Previous Steps | 88 | 53 | 41 |
| KL-015-19-F7 | Silica Gel Column Sub-Fraction of Pooled Active Fractions from Previous Steps | 60 | 43 | 29 |

TABLE 7-continued

Interaction of Valerian Sub-fractions with Human Dopamine D3 Receptors

| | | % Inhibition | | |
|---|---|---|---|---|
| Sample | Description | 100 µg/mL | 50 µg/mL | 25 µg/mL |
| KL-015-19-F8 | Silica Gel Column Sub-Fraction of Pooled Active Fractions from Previous Steps | 48 | 22 | 24 |
| KL-015-039-F2 | Preparatory TLC Fraction of Pooled Active Fractions from Previous Steps | 116 | 107 | 55 |

In summary, with regard to this example, it has been shown that Valerian inhibits ligand binding to the dopamine D3 receptor in a concentration dependent manner. Furthermore, the results of the bioactivity-guided fractionation indicate that there are compounds, or classes of compounds, from Valerian root extract that strongly interact with the dopamine D3 receptor.

EXAMPLE 4

Binding Potency of Further Purified Sub-fractions

Highly active sub-fractions were further purified and tested for their binding potency against the human dopamine D3 receptor, as outlined in Example 3. After full chemical characterization, active compounds were evaluated, as in Example 3. The results are shown in Table 8.

TABLE 8

Inhibition of Ligand Binding to the Human Dopamine D3 Receptor by Various Valerian Constituents

| Sample | Description | N | Conc. (µg/mL) | % Inhibition | Approximate | $EC_{50}$ |
|---|---|---|---|---|---|---|
| KL-015-040-F1 | Acetoxyvalerenic Acid MW 292 | 2 | 200 | 16 | >200 µg/mL | >685 µM |
| | | 2 | 100 | 1 | | |
| | | 2 | 50 | 10 | | |
| | | 2 | 25 | 3 | | |
| | | 2 | 12.5 | 7 | | |
| | | 2 | 6.25 | 1 | | |
| KL-015-025-F2 | Hydroxyvalerenic Acid MW 250 | 2 | 200 | 19 | >200 µg/mL | >800 µM |
| | | 2 | 100 | 17 | | |
| | | 2 | 50 | 0 | | |
| | | 2 | 25 | -3 | | |
| | | 2 | 12.5 | 21 | | |
| | | 2 | 6.25 | 2 | | |
| KL-015-039-F1 | Valerenic Acid MW234 | 2 | 200 | 109 | 45 µg/mL | 192 µM |
| | | 2 | 100 | 87 | | |
| | | 2 | 50 | 34 | | |
| | | 2 | 25 | 31 | | |
| | | 2 | 12.5 | 25 | | |
| | | 2 | 6.25 | 10 | | |
| VM-022-034-F1 | 10(14)-Aromadendren-4-ol MW 220 | 1 | 100 | 115 | 24.2 µg/mL | 110 µM |
| | | 1 | 33.3 | 66 | | |
| | | 1 | 11.1 | 15 | | |
| | | 1 | 3.7 | 4 | | |
| VM-022-034-F2 | 6, 10(14)-Guaiadien-4-ol MW 220 | 1 | 100 | 114 | 24.1 µg/mL | 110 µM |
| | | 1 | 33.3 | 66 | | |
| | | 1 | 11.1 | 15 | | |
| | | 1 | 3.7 | 5 | | |
| VM-022-034-F4 | Valerenol MW 220 | 1 | 100 | 119 | 10.5 µg/mL | 48 µM |
| | | 1 | 33.3 | 88 | | |
| | | 1 | 11.1 | 45 | | |
| | | 1 | 3.7 | 25 | | |
| VM-022-022-F1 | Degraded Valerenal | 1 | 100 | 31 | >100 µg/mL | NA |
| | | 1 | 33.3 | 31 | | |
| | | 1 | 11.1 | 21 | | |
| | | 1 | 3.7 | 18 | | |
| VM-022-033-F1 | Valerenal (VAL) MW 218 | 2 | 50 | 112 | 10.2 µg/mL | 47 µM |
| | | 2 | 25 | 94 | | |
| | | 2 | 12.5 | 49 | | |
| | | 2 | 6.25 | 26 | | |
| | | 2 | 3.13 | 25 | | |
| | | 2 | 1.56 | 7 | | |
| | | 2 | 0.78 | -8 | | |
| | | 2 | 0.39 | 10 | | |

TABLE 8-continued

Inhibition of Ligand Binding to the Human
Dopamine D3 Receptor by Various Valerian
Constituents

| Sample | Description | N | Conc. (μg/mL) | % Inhibition | Approximate | $EC_{50}$ |
|---|---|---|---|---|---|---|
| CB-001 | Volatile Oil (VO) | 1 | 100 | 104 | 19.5 μg/mL | NA |
|  |  | 1 | 33.3 | 55 |  |  |
|  |  | 1 | 11.1 | 32 |  |  |
|  |  | 1 | 3.7 | 21 |  |  |
| Combination | VA, AVA, VAL and VO (3:4:0.7:1); i.e. their ratio normally found in Valerian extracts | 1 | 100 | 77 | 30.2 μg/mL | NA |
|  |  | 1 | 33.3 | 59 |  |  |
|  |  | 1 | 11.1 | 13 |  |  |
|  |  | 1 | 3.7 | 18 |  |  |

The various articles and other references of the scientific and/or medical literature, and the U.S. and foreign patents and patent applications cited herein, including those listed below, are hereby incorporated by reference; each constitutes a part of the disclosure of this specification. Furthermore, while specific embodiments, working examples, and prophetic examples of the invention have been described in detail to illustrate the broad applicability and principles underlying the invention, it will be understood by those of skill in the art that the invention may be embodied otherwise without departing from such broad applicability and principles.

References

Boucher M A Restless legs syndrome in home healthcare. *Home Health Nurse* August 1997;15(8):551–6.

Fox G N Restless legs syndrome. *Am Fam Physician* January 1996;(1):147–52.

Grandjean P Restless legs syndrome—current aspects. *Schweiz Rundsch Med Prax* Apr. 30, 1997;86(18):732–6.

Hornyak M, Voderholzer U, Hohagen F, Berger M, Riemann D Magnesium therapy for periodic leg movements-related insomnia and restless legs syndrome: an open pilot study. *Sleep* Aug. 1, 1998;21(5):501–5.

Jones H J, Derodra J K Restless legs syndrome—a review. *Eur J Vasc Endovasc Surg* December 1997;14(6):430–2.

Joy M S Clonazepam: benzodiazepine therapy for the restless legs syndrome. *ANNA J* December 24;24(6):686–9.

Krueger B R Restless legs syndrome and periodic movements of sleep, *Mayo Clin Proc* July 1990;65(7):999–1006.

O'Keeffe S T Restless legs syndrome. A review. *Arch Intern Med* Feb. 12, 1996;156(3):243–8.

Silber M H Restless legs syndrome. *Mayo Clin Proc* March 1997;72(3):261–4.

Trenkwalder C, Walters A S, Hening W Periodic limb movements and restless legs syndrome. *Neurol Clin* August 1996;14(3):629–50.

Walters A S Toward a better definition of the restless legs syndrome. The International Restless Legs Syndrome Study Group. *Mov Disord* September 1995;10(5):634–42.

Wetter T C, Pollmacher T Restless legs and periodic leg movements in sleep syndromes. *J Neurol* April 1997;244(4 Suppl 1):S37–45.

Williams D C Periodic limb movements of sleep and the restless legs syndrome. *Va Med Q* 1996 Fall;123(4):260–5.

What is claimed is:

1. A method of treating the occurrence of at least one symptomology of at least one of the following disorders, Restless Leg Syndrome (RLS), periodic limb movements in sleep, periodic limb movement disorder, or the occurrence of unwanted limb movements, present in a host, comprising the step of:
administering to the host a pharmaceutically effective amount of one or more compounds of Valeriana selected from the group consisting of 10(14)-Aromadendren-4-ol, 6,10(14)-Guaiadien-4-ol, Valerenal, Valerenol, Valerenic acid, Acetoxyvalerenic acid, Hydroxyvalerenic acid and combinations thereof.

2. The method of claim 1, further comprising the step of identifying that the host is afflicted with Restless Leg Syndrome (RLS) or a related disorder.

3. The method according to claim 1, wherein said compound is isolated from an extract of Valeriana.

4. The method according to claim 3, wherein said compound is isolated from an extract of *Valeriana officinalis*.

5. The method according to claim 1, wherein said at least one symptomology is associated with insomnia in said host.

6. The method according to claim 1, wherein said host is a mammal.

7. The method according to claim 6, wherein said host is a human.

8. The method according to claim 6, wherein said host is a selected from the group consisting of canines, felines, and rodents.

9. The method according to claim 6, wherein said host is a mouse.

10. A method of inhibiting the occurrence of at least one symptomology of at least one of the following disorders, Restless Leg Syndrome (RLS), periodic limb movements in sleep, periodic limb movement disorder, or the occurrence of unwanted limb movements, present in a host, comprising the step of:
administering to the host a pharmaceutically effective amount of one or more compounds of Valeriana selected from the group consisting of 10(14)-Aromadendren-4-ol, 6,10(14)-Guaiadien-4-ol, Valerenal, Valerenol, Valerenic acid, Acetoxyvalerenic acid, Hydroxyvalerenic acid and combinations thereof.

11. The method according to claim 10, wherein said host is a mammal.

12. The method according to claim 11, wherein said host is selected from the group consisting of canines, felines, and rodents.

13. The method according to claim 11, wherein said host is a human.

14. The method according to claim 11, wherein said host is a rodent.

* * * * *